(12) United States Patent
Hill

(10) Patent No.: US 6,258,067 B1
(45) Date of Patent: Jul. 10, 2001

(54) MIDDLE EAR FLUID ASPIRATOR

(75) Inventor: Frank C Hill, Coumbia, SC (US)

(73) Assignee: Smith & Nephew, Inc., Bartlett, TN (US)

( * ) Notice: Subject to any disclaimer, the term of this patent is extended or adjusted under 35 U.S.C. 154(b) by 0 days.

(21) Appl. No.: 09/298,027

(22) Filed: Apr. 22, 1999

Related U.S. Application Data

(63) Continuation-in-part of application No. 09/207,695, filed on Dec. 8, 1998, now Pat. No. 6,024,726.

(51) Int. Cl.[7] ......................................................... A61M 5/00
(52) U.S. Cl. ........................... 604/187; 604/117; 604/239; 604/240; 604/540; 604/35
(58) Field of Search ........................................ 604/162, 163, 604/265, 187, 239, 240, 540, 317, 43, 44, 45, 117, 35, 181, 272, 149, 289, 294, 573; 600/576, 578, 579, 581

(56) References Cited

U.S. PATENT DOCUMENTS

| | | | |
|---|---|---|---|
| 3,055,361 | * | 9/1962 | Ballard . |
| 3,662,754 | * | 5/1972 | Halloran ................................ 604/162 |
| 4,891,332 | * | 1/1990 | Bloem et al. ......................... 438/384 |
| 5,032,111 | * | 7/1991 | Morris et al. ........................... 604/23 |
| 5,167,622 | * | 12/1992 | Muto ....................................... 604/35 |
| 5,188,617 | * | 2/1993 | Linder ................................... 604/232 |
| 5,201,718 | * | 4/1993 | Whisson ............................... 604/194 |
| 5,263,942 | * | 11/1993 | Smedley et al. ..................... 604/195 |
| 5,405,321 | * | 4/1995 | Reeves .................................... 604/44 |
| 5,792,099 | * | 8/1998 | DeCamp et al. ....................... 604/51 |
| 5,817,075 | * | 10/1998 | Giungo ................................. 604/294 |
| 5,865,814 | * | 2/1999 | Tuch ..................................... 604/265 |

* cited by examiner

*Primary Examiner*—Richard K. Seidel
*Assistant Examiner*—Jeremy Thissell
(74) *Attorney, Agent, or Firm*—Michael A Mann; Nexsen Pruet Jacobs & Pollard LLC

(57) ABSTRACT

A middle ear fluid aspirator comprised of a syringe assembly that provides suction through the creation of negative pressure therein and a needle having an angled region that permits the operation of the aspirator while maintaining visual contact with the tympanic membrane and a needle safety assembly whereby the penetrating portion of the needle is not capable of damaging the ossicular structures of the ear.

18 Claims, 3 Drawing Sheets

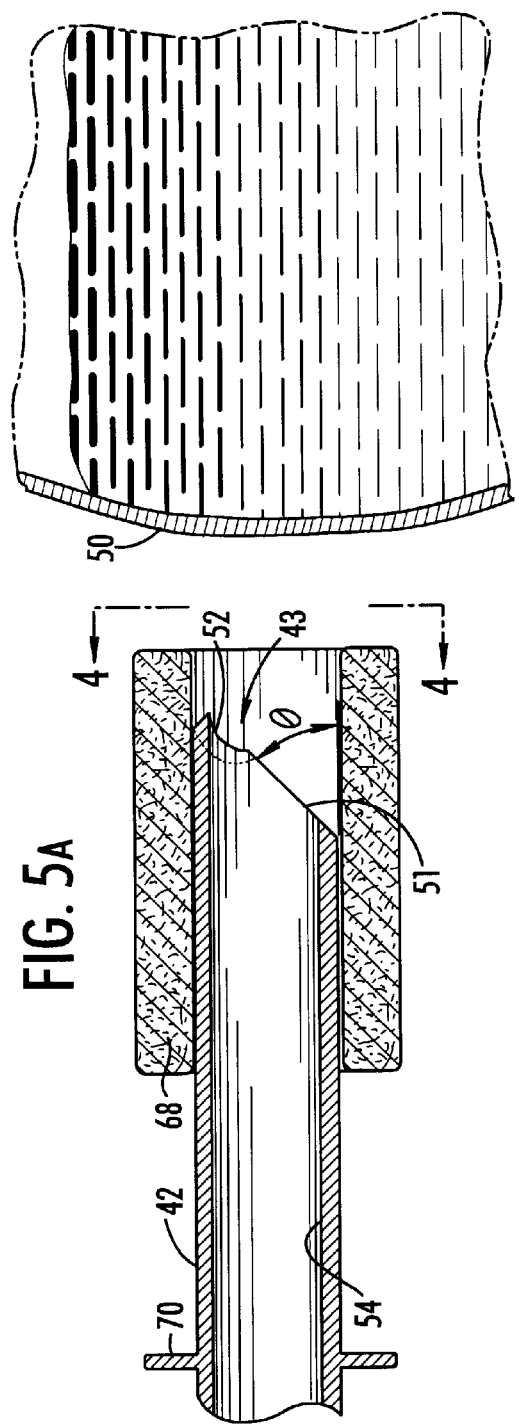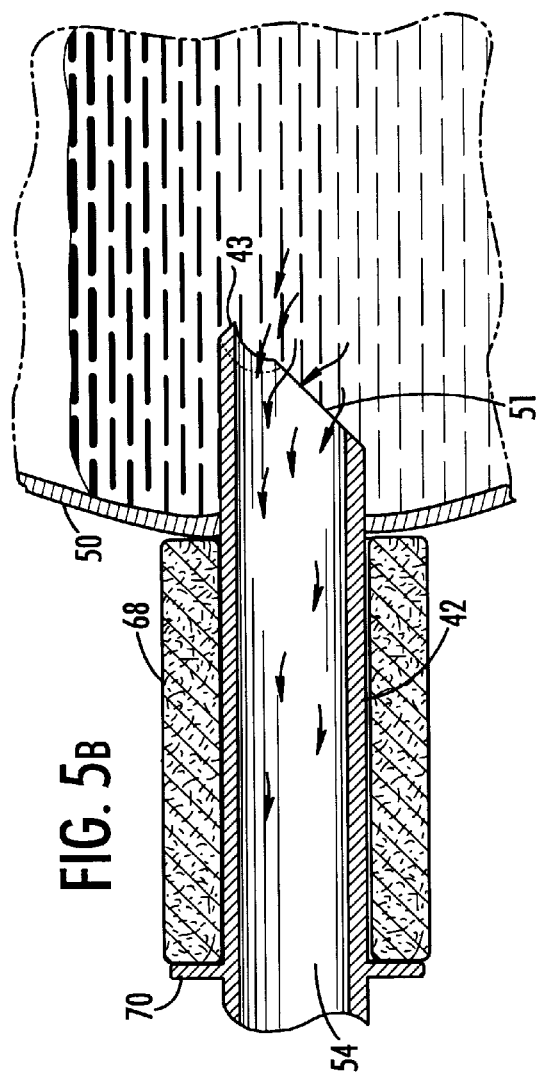
FIG. 5A
FIG. 5B

MIDDLE EAR FLUID ASPIRATOR

PRIORITY CLAIM

This application is a continuation-in-part of U.S. patent application Ser. No. 09/207,695, now U.S. Pat. No. 6,024,726 filed on Dec. 8, 1998.

FIELD OF THE INVENTION

The present invention relates to aspirators, and, in particular, to aspirators for removing fluid from the middle ear.

BACKGROUND OF THE INVENTION

Infections of the middle ear present an ongoing problem to both patients who suffer from them as well as to treating physicians who seek to treat them. To the patient, these infections represent acute pain, discomfort, financial cost and/or possible loss of hearing. To the treating physician, these infections present significant dilemmas. Since middle ear infections have been heretofore difficult to treat with medications, the treating physician had basically two therapeutic alternatives.

The primary care physician may either tap the middle ear or refer the patient to an ear, nose and throat specialist so that a tympanocentesis or insertion of tubes may be employed. In order to the tap the middle ear, the physician has utilized suction or conventional syringes which have several attendant disadvantages. Suction assemblies are often not available and are cumbersome to use. Conventional syringes have required the physician to actuate the syringe by pulling back on the plunger. Further, if the needle of the syringe is straight, as is usually the case, then the syringe interferes with the operator's line of vision. A common danger with pre-existing syringe needles is that there is no guard against the operator accidentally penetrating the tympanic membrane in such a way as to cause damage to the bony structures there within.

Therefore, there is a need for an aspirator with increased control that allows a clear line of sight with the tympanic membrane and includes safety features which prevents damage to the ear canal and middle ear structures.

SUMMARY OF THE INVENTION

In view of the foregoing, a present invention is a middle ear fluid aspirator comprising a syringe assembly and needle. The syringe assembly operates via negative pressure in order to provide suction through the needle when the syringe handle is pushed. The needle has an angled or curved region, which permits the operator to use the aspirator while having visual contact with the tympanic membrane. The needle has a fibrillar sheath that shields the sharp tip of the needle to prevent injury while entering the ear canal and retracts upon contact with the tympanic membrane. The sheath may also act as a carrier for anesthetic. A stop is also positioned on the needle to restrict movement of the sheath, thereby helping to limit penetration of the needle. The tip of the needle preferably has a shallow bevel to prevent lateral contact with the medial wall of the middle ear. Preferably, the needle has thin walls that deform when it contacts bone.

A syringe assembly that is actuated by pushing on the handle is a major advantage of present invention. With a physician being able to push the syringe handle rather than pull, the aspirator can be operated with a single hand with greater control with a single hand since the muscles that control the hand can squeeze the thumb toward the rest of the hand more easily than pull it away from the hand.

An important advantage of the present invention is ability to have a clear line of sight with the tympanic membrane. In accordance with this advantage, the needle has a curved portion so that the syringe handle does not obstruct the view of the tip of the syringe. Moreover, the amount of suction delivered to the needle tip is proportional with the rate at which the plunger is pressed.

A major feature of the present invention is the sheath that shields the needle tip until contact with the tympanic membrane. The sheath creates a safety advantage by preventing injury to the ear canal when introducing the needle into the ear. A secondary feature of the sheath is its use as a carrier for anesthetic, or other fluid to be applied to the tympanic membrane. As a result of the carrier function, the fluid can be applied to the tympanic membrane in one step, without the need to introduce another instrument into the ear. Moreover, the sheath acts as a seal around the puncture site while permitting the withdrawal of fluid through the needle to prevent aspiration of air from the ear canal instead of fluid from the middle ear.

An important feature of the present invention is a stop that acts in conjunction with the sheath to limit penetration of the needle. As a result, the physician can be assured that the needle will be prevented from penetrating too far and damaging middle ear structures.

The shallow bevel of the needle tip is another feature of the present invention. Since the middle ear is a shallow structure, the shallow bevel allows sufficient penetration of the needle to allow aspiration of fluid while preventing aspiration of air from the ear canal.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

FIG. 5A is a cross-sectional view of the needle carrying a sheath prior to penetration of the tympanic membrane, according to a preferred embodiment of the present invention; and FIG. 5B is a cross-sectional view of the needle carrying a sheath upon penetration of the tympanic membrane, according to a preferred embodiment of the present invention.

DESCRIPTION OF THE PREFERRED EMBODIMENTS

Figure 1:
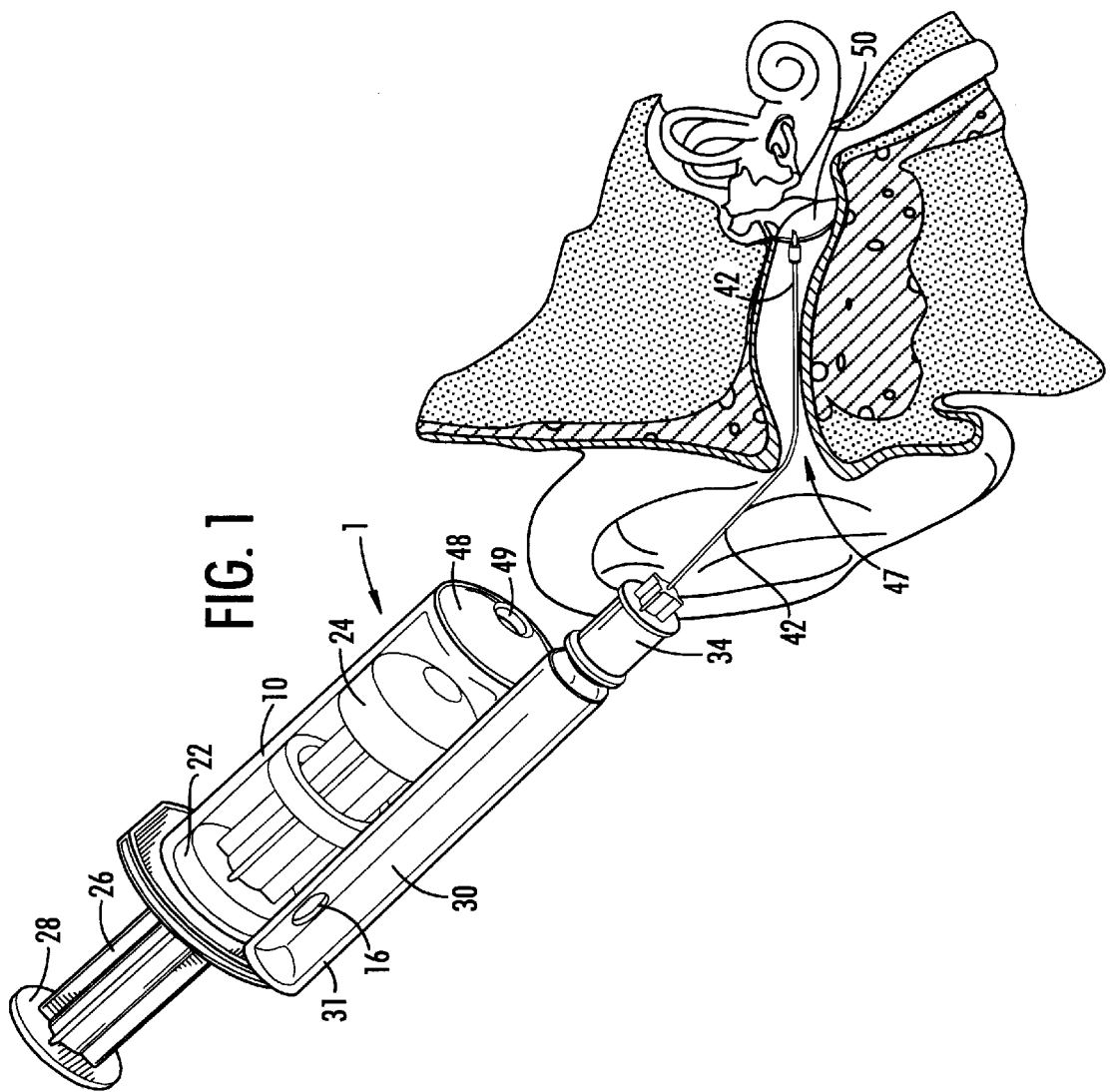
FIG. 1 is a perspective view of the middle ear fluid aspirator inserted through the tympanic membrane of a patient, according to a preferred embodiment of the present invention.

With reference to FIG. 1, the syringe assembly of the present invention is identified by the numeral 1 and is shown in place within the ear canal 47 of a patient. The tip 43 of the syringe needle 42 is shown penetrating the tympanic membrane 50 so that fluid accumulated within the middle ear may be extracted by use of syringe 1. Needle 42 draws fluid from the middle ear into a second compartment 30 of housing 10 when tip 43 penetrates tympanic membrane 50 and a handle 28 is pressed with the user's thumb, driving shaft 26 into housing 10.

Figure 2:
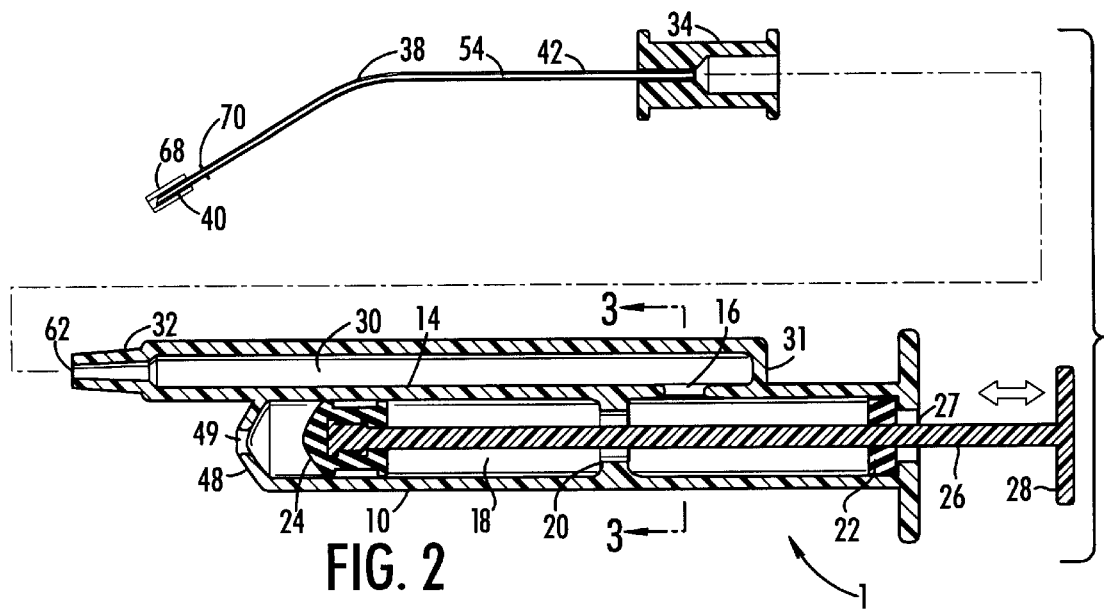
FIG. 2 is an exploded cross-sectional view middle ear fluid aspirator, according to a preferred embodiment of the present invention.

With reference to FIG. 2, syringe assembly 1 is comprised of a housing 10, a partition 14, dividing the housing 10 into a first compartment 18 and a second compartment 30, an opening 16 allowing first compartment 18 to communicate with second compartment 30, a piston 24, disposed in first compartment 18 and attached to shaft 26, a first end wall 48 having a port 49 that is disposed at the end of first compartment 18, a seal means 22, a slide stop 20, and a needle hub 32 carried on second compartment 30.

The housing 10 generally cylindrical in shape and may be made of any suitable, and preferably translucent, material such as glass, plastic, or the like. Housing 10 is divided into a first compartment 18 and second compartment 30 by partition 14. First end wall 48 has a port 49 for the egress of air when handle 28 is pressed, and a second end wall 31 and seal means 22 which may be a natural or synthetic rubber or plastic ring. First compartment 18 is connected to second compartment 30 by opening 16. Disposed within first compartment 18 is piston 24 which is attached to shaft 26. Shaft 26 extends through seal means 22 and through aperture 27 and is attached to handle 28. As the operator applies pressure to handle 28, shaft 26 forces piston 24 to move from an initial position adjacent to and in contact with slide stop 20 towards end wall 48. Such movement causes negative pressure behind piston 24 and thereby causes fluid flow into second compartment 30 through opening 16. Piston 24 and seal means 22 are made of any suitable material which is inert to the aspirated fluid and provides a sufficiently airtight seal with the walls of first compartment 18 and slidable seal with shaft 26 such that piston 24 can be moved in and out of housing 10 and create sufficient negative pressure inside first compartment 18 to aspirate fluid into second compartment 30.

Needle hub 32 provides a location for frictionally fitting needle anchoring means 34 such that needle 42 may be attached to syringe assembly 1 at needle hub 32 in an airtight fashion in which the lumen 54 of needle 42 is in fluid communication with second compartment 30 for flow of fluids from lumen 54 through aperture 27 into second compartment 30. Needle 42 is provided with angled or curved region 38 allowing insertion of needle 42 into ear canal 49 of a patient while allowing the user visual access to the tympanic membrane 50 while sighting along needle 42 towards its tip 43 while holding handle 28 to the side where it is not in the line of sight. Angled region 38 is bent to a suitable degree for use with an otoscope, and may range from about 60° to about 30°, preferably about 45°.

Figure 3:
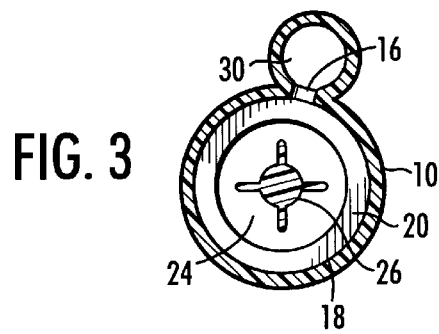
FIG. 3 is a cross-sectional view of the syringe assembly of the middle ear aspirator of the present invention along the 3—3 line of FIG. 2, according to a preferred embodiment of the present invention.
Figure 4:
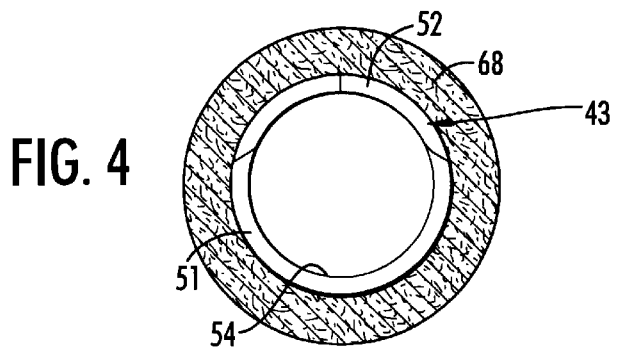
FIG. 4 is a cross-sectional view of the needle carrying a sheath along line 4—4 of FIG. 5A, according to a preferred embodiment of the present invention.

With reference to FIG. 3, a cross-sectional view of syringe assembly 1 along axis 3 wherein first compartment 18 is shown in relationship to second compartment 30 within housing 10. In first compartment 18 slide stop 20 can be seen. Extending therethrough is shaft 26 which is anchored to piston 24.

As best seen in FIG. 5A, needle 36 has a shallow bevel 51, which prevents aspiration of air from ear canal 47 but allows easy penetration of the tympanic membrane for aspiration of fluid from the middle ear. By the term shallow, it is meant that the bevel angle, represented by θ, is more than a few degrees and preferably approximately 45°. The needle tip 43 has a second bevel, a counter-bevel portion 52, which provides a sharp tip 43 to enable easy penetration of the tympanic membrane 50. Preferably only the needle tip 43 has a counter-bevel portion 52, rather than the entire bevel 51. As a result, the counter-bevel portion 52 allows for initial penetration, but the remaining bevel 51 acts to stretch the tympanic membrane 50, rather than cut tissues.

Needle tip 43 carries a sheath 68 primarily to prevent injury to the ear canal 47 when the needle 42 is introduced into the ear. Sheath 68 is preferably made from a fibrillar or foamy material, such as that sold under the trademarks Gel Foam or Dacron, would be suitable material for sheath 68. Sheath 68 shields ear canal from injury during introduction into ear as seen in FIG. 5A; however, upon sheath 68 contact with tympanic membrane 50, sheath 68 moves axially from a first, needle tip-covering position to a second, needle tip exposing position to allow penetration as seen in FIG. 5B. Stop 70, which defines the second position, restricts axial movement of sheath 68 and thereby helps to prevent excessive penetration of tip 43, as illustrated in FIG. 5B. Stop 70 is positioned along needle 42 to allow retraction of sheath 68 while limiting penetration of needle 42. A secondary function of sheath 68 is a use as a carrier for delivering a material to the tympanic membrane 50, such as an anesthetic and/or antiseptic solution (not shown).

In use, needle 42 is inserted into ear canal 47 with sheath 68 carried on it to shield needle tip 43 to prevent injury to the ear canal 47. Upon sheath 68 contact with the tympanic membrane 50, sheath 68 slides axially by pressure of the tympanic membrane to stop 70, to allow exposure and penetration of needle tip 43 into tympanic membrane 50. The physician or user pushes handle 28 toward needle 42 to aspirate fluid from the middle ear.

While the present invention has been described with respect to embodiments, it will be understood that various modifications and variations will occur to those skilled in the art from the foregoing detailed description and the accompanying drawings. Such modifications and variations are intended to fall within the scope of the appended claims.

What is claimed is:

1. An aspirator for extracting fluids from a middle ear, said aspirator comprising:
    a housing having a compartment and an aperture;
    a needle carried by said housing at said aperture, said needle having a tip, said needle having a bore extending longitudinally therethrough, said bore being in fluid communication through said aperture with said compartment;
    a handle carried by said housing and movable with respect to said housing, said needle having a curved portion so that a user can sight down said needle toward said tip while holding said handle to the side;
    a sheath carried by said needle, said sheath movable axially between a first position that shields said tip of said needle and a second position that exposes said tip, said sheath moving from said first to said second positions when said sheath meets resistance; and
    extraction means responsive to movement of said handle with respect to said housing for applying a negative pressure to said compartment so that, when said needle penetrates said middle ear and said handle is moved toward said needle, said fluid is drawn through said needle into said compartment.

2. The aspirator as recited in claim 1, wherein said sheath is capable of delivering an anesthetic.

3. The aspirator as recited in claim 1, wherein said needle tip has a double bevel.

4. The aspirator as recited in claim 1, wherein said needle carries a stop that defines said second position.

5. The aspirator as recited in claim 1, wherein said curved portion is angled between 30 to 60 degrees.

6. The aspirator as recited in claim 1, wherein said curved portion is angled at approximately 45 degrees.

7. The aspirator as recited in claim 1, wherein said needle is formed to deform upon contact of said needle with bone but not with an ear drum.

8. An aspirator for extracting fluids from a middle ear, said aspirator comprising:

a housing having a compartment and an aperture;

a needle carried by said housing at said aperture, said needle having a beveled tip, said needle having a bore extending longitudinally therethrough, said bore being in fluid communication through said aperture with said compartment;

a handle carried by said housing and movable with respect to said housing;

a fibrillar sheath carried by said needle, said sheath movable axially between a first position that shields said tip of said needle and a second position that exposes said tip, said sheath moving from said first to said second positions when said sheath meets resistance; and extraction means responsive to movement of said handle with respect to said housing for applying a negative pressure to said compartment so that, when said needle penetrates said middle ear and said handle is moved toward said needle, said fluid is drawn through said needle into said compartment.

9. The aspirator as recited in claim 8, wherein said sheath is capable of delivering an anesthetic.

10. The aspirator as recited in claim 8, wherein said curved portion is angled between 30 to 60 degrees.

11. The aspirator as recited in claim 8, further comprising means for controlling the negative pressure within said compartment.

12. An aspirator for extracting fluids from a middle ear, said aspirator comprising:

a housing having a compartment and an aperture;

a needle carried by said housing at said aperture, said needle having a beveled tip, said needle having a bore extending longitudinally therethrough, said bore being in fluid communication through said aperture with said compartment, said needle being formed to deform upon contact of said needle with bone but not with an ear drum;

a handle carried by said housing and movable with respect to said housing;

a fibrillar sheath carried by said needle, said sheath movable axially between a first position that shields said tip of said needle and a second position that exposes said tip, said sheath moving from said first to said second positions when said sheath meets resistance; and extraction means responsive to movement of said handle with respect to said housing for applying a negative pressure to said compartment so that, when said needle penetrates said middle ear and said handle is moved, said fluid is drawn through said needle into said compartment.

13. An aspirator for extracting fluids from a middle ear, said aspirator comprising:

a housing having a compartment and an aperture;

a needle carried by said housing at said needle having a bore extending longitudinally therethrough, said bore being in fluid communication through said aperture with said compartment;

a sheath carried by said needle, said sheath movable axially between a first position that shields said tip of said needle and a second position that exposes said tip, said sheath moving from said first to said second positions when said sheath meets resistance;

a handle carried by said housing and movable with respect to said housing, said needle having a curved portion so that a user can sight down said needle toward said tip while holding said handle to the side; and extraction means responsive to movement of said handle with respect to said housing for applying a negative pressure to said compartment so that, when said needle penetrates said middle ear and said handle is moved toward said needle, said fluid is drawn through said needle into said compartment.

14. The aspirator as recited in claim 13, wherein said sheath is capable of carrying an anesthetic.

15. The aspirator as recited in claim 13, wherein said needle carries a stop that defines said second position.

16. The aspirator as recited in claim 13, wherein said curved portion is angled between 30 to 60 degrees.

17. The aspirator as recited in claim 16, wherein said curved portion is angled at approximately 45 degrees.

18. The aspirator as recited in claim 13, wherein said needle is formed to deform upon contact of said needle with bone but not with an car drum.

* * * * *